US012648954B2

(12) United States Patent
Bruun et al.

(10) Patent No.: US 12,648,954 B2
(45) Date of Patent: *Jun. 9, 2026

(54) CANNABINOID LOZENGE FORMULATION

(71) Applicant: NordicCan A/S, Vejle (DK)

(72) Inventors: Heidi Ziegler Bruun, Vejle Ost (DK); Dorthe Schackinger Boesen, Vejle (DK); Ane Eriksen, Vejle (DK)

(73) Assignee: NORDICCAN A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/559,598

(22) Filed: Dec. 22, 2021

(65) Prior Publication Data

US 2022/0110912 A1      Apr. 14, 2022

Related U.S. Application Data

(63) Continuation of application No. 16/852,133, filed on Apr. 17, 2020, now Pat. No. 11,241,413.

(30) Foreign Application Priority Data

Apr. 17, 2019    (CA) ...................................... 3040547

(51) Int. Cl.
| | |
|---|---|
| *A61K 31/00* | (2006.01) |
| *A61K 9/00* | (2006.01) |
| *A61K 47/02* | (2006.01) |
| *A61K 47/26* | (2006.01) |
| *A61K 47/38* | (2006.01) |
| *A61K 47/40* | (2006.01) |

(52) U.S. Cl.
CPC .......... *A61K 31/658* (2023.05); *A61K 9/0056* (2013.01); *A61K 47/02* (2013.01); *A61K 47/26* (2013.01); *A61K 47/38* (2013.01); *A61K 47/40* (2013.01)

(58) Field of Classification Search
CPC ....... A61K 9/0056; A61K 31/05; A61K 47/26
See application file for complete search history.

(56) References Cited

U.S. PATENT DOCUMENTS

| | | | |
|---|---|---|---|
| 6,730,330 B2 | 5/2004 | Whittle et al. | |
| 8,735,374 B2 | 5/2014 | Zerbe et al. | |
| 9,308,175 B2 * | 4/2016 | Pellikaan ................. | A61K 9/10 |
| 10,137,161 B2 | 11/2018 | Kolsky | |
| 10,434,084 B2 * | 10/2019 | Raber et al. ......... | A61K 31/352 |
| 2010/0034888 A1 | 2/2010 | Pellikaan et al. | |
| 2012/0276199 A1 | 11/2012 | Bondu et al. | |
| 2016/0015683 A1 * | 1/2016 | McCarty .............. | A61K 31/352 |
| 2016/0220593 A1 * | 8/2016 | Anastassov .......... | A61K 31/704 |

| | | | |
|---|---|---|---|
| 2017/0157041 A1 | 6/2017 | Goldner | |
| 2017/0368020 A1 | 12/2017 | Estey et al. | |
| 2018/0042842 A1 | 2/2018 | Whittle et al. | |
| 2018/0071350 A1 | 3/2018 | Kolsky | |
| 2018/0169035 A1 * | 6/2018 | Eyal ..................... | A61K 31/015 |
| 2018/0193392 A1 | 7/2018 | Silver | |
| 2018/0221304 A1 | 8/2018 | Small-Howard et al. | |
| 2020/0061022 A1 | 2/2020 | Nowak et al. | |
| 2020/0316012 A1 | 10/2020 | Schou | |

FOREIGN PATENT DOCUMENTS

| | | | | |
|---|---|---|---|---|
| CA | 2664311 C | 8/2015 | | |
| CA | 3028973 A1 | 12/2017 | | |
| EP | 2298284 A2 * | 3/2011 | ............. | A61K 9/127 |
| EP | 2061427 B1 | 7/2011 | | |
| WO | 2004096184 A1 | 11/2004 | | |
| WO | 2009134947 A1 | 11/2009 | | |
| WO | 2013169101 A1 | 11/2013 | | |
| WO | 2016126592 A1 | 8/2016 | | |
| WO | 2017183011 A1 | 10/2017 | | |
| WO | 2017202424 A1 | 11/2017 | | |
| WO | 2017223309 A1 | 12/2017 | | |
| WO | 2018022669 A1 | 2/2018 | | |
| WO | 2018089863 A1 | 5/2018 | | |
| WO | 2018142403 A1 | 8/2018 | | |
| WO | 2018144637 A1 | 8/2018 | | |

OTHER PUBLICATIONS

Lumír Ondřej Hanuš, Terpenes/Terpenoids in Cannabis: Are They Important?, Med Cannabis Cannabinoids 2020;3:25-60 (Year: 2020).*
Do Terpenes Classify as Lipids? Terpene Classification, Floraplex Terpenes, downloaded in Nov. 2023 (Year: 2023).*
Wade et al., "A multicentre, randomised, double-blind, single-dose study assessing the efficacy of AMC/DCBA Warm ozenge or AMC/DC BA Cool lozenge in the relief of acute sore throat", pub. date: Feb. 18, 2011 (Year: 2011).
Link et al., "Fluidized bed spray granulation: Investigation of the coating process on a single sphere", publication date: Dec. 1997 (Year: 1997).
International Search Report and Written Opinion for International Application No. PCT/DK2020/050098 dated Jul. 17, 2020.
Kinghorn, et al. (editors), Phytocannabinoids, vol. 103, Progress in the Chemistry of Organic Natural Products, Contents, "Phytochemistry of *Cannabis sativa* L." written by Mahmoud A. ElSohly, et al., 34 pages, Springer International Publishing, Switzerland, 2017.

* cited by examiner

*Primary Examiner* — Robert A Wax
(74) *Attorney, Agent, or Firm* — Harris Beach Murtha Cullina PLLC

(57)      ABSTRACT

The present invention relates to a lozenge composition for controlled release of cannabinoids containing i) a master granule component including one or more solid particles and one or more cannabinoids reversibly associated with the one or more solid particles; and ii) an extragranular component blended with the master granule component that includes one or more extragranular sugar alcohols.

23 Claims, No Drawings

CANNABINOID LOZENGE FORMULATION

FIELD OF THE INVENTION

The invention relates to the field of cannabinoids and alleviation or treatment of a condition with one or more cannabinoids. In particular, the invention relates to lozenges for oral administration of one or more cannabinoids. More specifically, the invention relates to formulation designs that are particularly useful for administration of one or more cannabinoids.

BACKGROUND OF THE INVENTION

Cannabinoid delivery methods have been the attention of more and more interest in recent years. Lung delivery is most commonly achieved by smoking *Cannabis*. However, there are health concerns for this mode of administration. *Cannabis* smoke carries even more tars and other particulate matter than tobacco. Furthermore, many patients find the act of smoking unappealing, as well as being generally unhealthy. For these reasons, smoking *Cannabis* is not acceptable as a medical means of administration.

Cannabinoids are a group of chemicals found in *Cannabis sativa, Cannabis indica, Cannabis ruderalis*, Marijuana plant and related plant species. They are known to activate cannabinoid receptors (CB1 and CB2). These chemicals are also produced endogenously in humans and other animals. Cannabinoids are cyclic molecules exhibiting particular properties such as being lipophilic, have the ability to easily cross the blood-brain barrier, and having low toxicity.

*Cannabis sativa* contains more than 400 chemicals and approximately 120 cannabinoids, the active constituents of *Cannabis*, including tetrahydrocannabinol (THC), cannabidiol (CBD), cannabinol (CBN), tetrahydrocannabivarin (THCV) and cannabigerol (CBG). Pharmacologically, the principal psychoactive constituent of *Cannabis* is tetrahydrocannabinol (THC), which is used for treating a wide range of medical conditions, including glaucoma, AIDS wasting, neuropathic pain, treatment of spasticity associated with multiple sclerosis, fibromyalgia and chemotherapy-induced nausea. THC is also effective in the treatment of allergies, inflammation, infection, depression, migraine, bipolar disorders, anxiety disorder, drug dependency and drug withdrawal syndromes.

Attempts have been made to overcome some of the problems associated with smoking both *Cannabis* and tobacco by providing various smokeless inhalable aerosol formulations for lung delivery. These formulations were found to be of varying effectiveness in delivering the active agent to the lungs and compliance was an issue even with proper training on the use of inhalation devices.

Oral administration is the easiest and most convenient route of administration. However, cannabinoids are highly lipophilic, meaning that they are soluble in lipids and some organic solvents while being substantially insoluble or only sparsely soluble in water. Cannabinoids are soluble in highly non-polar solvents. Some of these solvents are pharmaceutically unacceptable, and the pharmaceutically acceptable solvents need to be used in high concentrations to produce solutions.

In formulating lozenges, various challenges are associated with obtaining a homogenous mixture where variations are avoided and a safe and convenient delivery may be obtained. Also, the general formulation of the lozenges offering convenience to the user need not be compromised which is often the case if conventional delivery means are applied. This implies that it is an advantage to formulate delivery systems with components that are already present in the lozenge formulation or that may promote additional benefits to the user without adding ingredients that are either pharmacologically inacceptable or complex in nature.

Furthermore, it is preferable that a formulation is provided that may also help in obtaining a release profile of cannabinoids that offers increased convenience and effectiveness. In general, less attention is given in the prior art on the impact of the lozenge formulation for the sensorics properties of oral cannabinoid delivery. Here, important sensorics properties include friability, texture, flavor perception, sweetness perception and off-notes associated with cannabinoids. These properties are both relevant from a convenience perspective in lozenges, but certainly also in order to support an appropriate delivery of cannabinoids from lozenges and avoid adverse side effects of cannabinoids.

One of the challenges with lozenges as a delivery vehicle of cannabinoids is that cannabinoids tend to be associated with off-notes during administration due to the specific physiochemical properties of the compounds. The taste masking challenge is more profound when a higher release of cannabinoids are delivered by such lozenges. If off-notes are the predominant sensation during administration, convenience may be affected and even more critically, the delivery of cannabinoids may also be affected. Saliva production may be suppressed, and the delivery vehicle may not be handled correctly.

Hence, there is a need in the prior art for improved lozenge formulations that solve the above-referenced challenges and problems of the prior art. In particular, there is a need in the prior art for new lozenge platforms for use in lozenges that support appropriate delivery of cannabinoids combined with beneficial sensorics properties.

SUMMARY OF THE INVENTION

Accordingly, there is provided a lozenge composition for controlled release of cannabinoids comprising a master granule component comprising one or more solid particles and one or more cannabinoids reversibly associated with the one or more solid particles; and an extragranular component blended with the master granule component comprising one or more extragranular sugar alcohols.

Providing a lozenge formulation according to the invention may solve various problems of the prior art and aims at establishing a lozenge formulation that combines beneficial delivery properties of cannabinoids combined with advantageous sensorics properties. Additionally, the specific application of a master granule component in combination with an extragranular component aims at further improving the delivery vehicle according to the invention.

With respect to release properties, the present invention may offer an improved release profile of cannabinoids compared to conventional lozenge formulations. In particular, the specific lozenge formulation platform of the present invention may serve to provide improved release characteristics of cannabinoids compared to conventional lozenge formulation platforms applied in combination with cannabinoids.

In addition, the present invention may serve to provide controlled release of cannabinoids such that the lozenge formulation is tailored to deliver an effective content of cannabinoids over time and at the same time avoid adverse effects of cannabinoids, such as off-notes.

A very important aspect of the present invention is the provision of beneficial sensorics properties. Here, important sensorics properties include friability, texture, flavor perception, sweetness perception and off-notes associated with cannabinoids. These properties are both relevant from a convenience perspective in lozenges, but certainly also in order to support an appropriate delivery of cannabinoids from a lozenge formulation, such as an improved release profile, and avoid adverse side effects of cannabinoids.

The present inventors have shown very surprising results with the specific combination of features of the present invention in terms of these sensorics properties. It was an unexpected result that the invention could both contribute to an improved release profile, such as rapid release of cannabinoids, and at the same time provide very beneficial sensorics properties which in terms may also support an appropriate delivery of cannabinoids from lozenges and avoid adverse side effects of cannabinoids.

One of the sensorics properties that are particularly advantageous is friability of the lozenge tablet. Both in order to secure a desired release of cannabinoids and to improve the sensation by a consumer, it is critical that friability is balanced. Also, the texture of the lozenge formulation during use is critical for the release of cannabinoids and the experience as well as convenience during use. These properties may be improved by the present invention which was not expected by the inventors of the present invention.

Certain observations of the inventors was that the master granule of the invention may impact the friability of a lozenge tablet. Hence, in general terms the balance of the master granule component and extragranular component may have an impact on the friability of the lozenge tablet. Additionally, other sensorics properties may also be affected by the balance of these components. Hence, apart from the delivery benefits of the components, the components are also associated with further benefits in terms of sensorics properties.

Advantageously, the compositions of the present invention can be formulated in much smaller lozenges than traditional cannabinoid containing lozenges and, thus, may have reduced dissolution times in the oral cavity while still achieving significant cannabinoid plasma level and obtaining comparable cannabinoid pharmacokinetic profiles to the traditional lozenge. By reducing dissolution time and improving the speed of cannabinoid absorption, patient compliance may also be improved.

In an embodiment of the invention, the weight ratio of the master granule component relative to the one or more extragranular sugar alcohols is from 1:30 to 1:2.

The master granule component may serve to obtain a more homogeneous mixture of cannabinoids in addition to the aforementioned benefits. However, due to the nature of the granules, such as friability properties, it may in some embodiments be an advantage that the master granule component is only present in an amount less than the amount of extragranular sugar alcohols. On the other hand, it may be an advantage to have a certain amount of the master granule components to secure a homogeneous mixture of the lozenges.

In an embodiment of the invention, the weight ratio of the master granule component relative to the one or more extragranular sugar alcohols is from 1:20 to 1:3.

In an embodiment of the invention, the weight ratio of the master granule component relative to the one or more extragranular sugar alcohols is from 1:10 to 1:4.

In some embodiments of the invention, the weight ratio of the master granule component relative to the one or more extragranular sugar alcohols is from 1:15 to 1:3. In some embodiments of the invention, the weight ratio of the master granule component relative to the one or more extragranular sugar alcohols is from 1:20 to 1:2.

In the present context, the "master granule component" is intended to mean a component that is distinguishable from the "extragranular component". The "master granule component" is a component that is typically pre-prepared and incorporates one or more cannabinoids before incorporation with the other ingredients of the lozenge, such as pretreatment by wet-granulation or premixture. The intention with the "master granule component" is to achieve benefits of the lozenge, such as a controlled release and dissolution profile of the lozenge tablet, or improved sensorics properties, such as friability or off-note masking, or a more homogeneous product.

Generally, the "master granule component" is distributed evenly in the lozenge formulation with the "extragranular component" distributed in areas around the "master granule component". Further components may be present in the lozenge formulation. In the present context ingredients that are merely granulated without presence of cannabinoids are not considered part of the "master granule component" but may be considered part of the "extragranular component".

In the present context the wording "cannabinoids reversibly associated with the one or more solid particles" or similar wording is intended to mean that the one or more cannabinoids are in contact with the one or more solid particles and are not loosely distributed within the master granule component. During storage of the lozenge composition and during storage of a lozenge, the one or more cannabinoids are generally associated with the one or more solid particles. This may be in form of physical attachment, encapsulation, incorporation, solution, chemical interactions, or the like. However, during use in the oral cavity in contact with saliva, the intention is that the cannabinoids may be detached or released from the one or more solid particles, so that the one or more cannabinoids may target mucosal surfaces. The meaning of "reversibly" is therefore intended to mean that the one or more solid particles work as a means to carry the one or more cannabinoids before use and to secure delivery of the one or more cannabinoids. Also, the one or more solid particles may work to secure a microenvironment that may provide a more stable composition. Furthermore, the one or more solid particles may secure that the one or more cannabinoids are targeted to their site of action, i.e. the mucosal membrane.

In an embodiment of the invention, the one or more extragranular sugar alcohols are directly compressible (DC) sugar alcohols.

Due to the sensorics properties, it may in some embodiments be an advantage to apply directly compressible (DC) sugar alcohols in the extragranular component. For instance, when a cannabinoid oil suspension is used in the extragranular component, the tablet structure may be different than if a solid cannabinoid is used. In this case, it may be an advantage to apply directly compressible (DC) sugar alcohols in the extragranular component. The friability may be more suitable if directly compressible (DC) sugar alcohols are applied in the extragranular component.

In an embodiment of the invention, the one or more solid particles are agglomerated to form a granule together with the one or more cannabinoids.

Granules are preferred in some embodiments. A common problem associated with transmucosal administration via the buccal route is swallowing due to the continuous secretion of saliva in the oral cavity. For optimal drug delivery, the lozenge formulation may preferably remain in contact with oral mucosa for a time sufficient to allow for the absorption of the one or more cannabinoids. More specifically, lozenge formulation may preferably not be washed away by saliva into the gastrointestinal tract if buccal absorption is the target. However, the rate of disintegration or dissolution of the lozenge formulation may preferably not be so slow as to cause discomfort or inconvenience for the patient. Additionally, suitable lozenge formulation may preferably be small in size and designed so that the shape avoids discomfort to the patient during use. Most importantly the formulation may preferably be designed so that the cannabinoid is in a solution which optimizes its transmucosal permeation. These considerations may be obtained with the master granular component of the present invention.

In an embodiment of the invention, the granule is obtained through wet granulation.

In an embodiment of the invention, the granule is obtained through dry granulation.

In an embodiment of the invention, the master granule component is a premixture of the one or more solid particles and the one or more cannabinoids.

In the present context, a "premixture" is intended to mean that the one or more cannabinoids have been mixed with the one or more solid particles prior to being applied in the lozenge formulation together with the extragranular component.

In the present context, a premixture is partly used to allocate the one or more cannabinoids properly to the manufacturing process and secure that the uniformity is not compromised and that the cannabinoids are distributed properly into the mixture. Preferably, the cannabinoids are provided in a premixture with one or more sugar alcohols. It was a surprise to the inventors that a premixture was important to have in order for the cannabinoids to be distributed properly in the manufacturing process and to end up with a product where the uniformity was consistent.

In an embodiment of the invention, the master granule component is a premixture of the one or more solid particles and the one or more cannabinoids reversibly adsorbed onto the one or more solid particles.

In an embodiment of the invention, the master granule component comprises one or more cannabinoid solvents into which the one or more cannabinoids are solvated, such as glycol, alcohol or alkyl solvents or mixtures thereof. This may for instance be the case where an isolated cannabinoid is applied, such as a solid isolated cannabinoid.

In an embodiment of the invention, the one or more cannabinoid solvents are selected from the group consisting of polyethylene glycol, ethanol, substituted polyethylene glycols, diethylene glycol monoethyl ether, propylene glycol, propylene carbonate, or a mixture thereof.

In an embodiment of the invention, the master granule component comprises one or more cannabinoid lipid carriers into which the one or more cannabinoids are located.

In an embodiment of the invention, the master granule component comprises one or more cannabinoid oil carriers into which the one or more cannabinoids are located.

In an embodiment of the invention, the master granule component comprises one or more cannabinoid fat carriers into which the one or more cannabinoids are located.

In an embodiment of the invention, the one or more cannabinoid lipid carriers comprise one or more cannabinoid extracts.

In an embodiment of the invention, the one or more cannabinoid lipid carriers comprise one or more terpenes.

In an embodiment of the invention, the one or more terpenes are selected from the group consisting of bisabolol, borneol, caryophyllene, carene, camphene, cineol, citronella, eucalyptol, geraniol, guaiol, humulene, isopropyltoluene, isopulegol, linalool, limonene, menthol, myrcene, nerolidol, ocimene, pinene, phytol, pulegone, terpinene, terpinolene, thymol, salts thereof, derivatives thereof, and mixtures of terpenes.

In an embodiment of the invention, the one or more cannabinoid lipid carriers comprise one or more fatty acids.

In an embodiment of the invention, the one or more cannabinoid lipid carriers comprise one or more glycerols.

In an embodiment of the invention, the one or more cannabinoid lipid carriers comprise one or more waxes.

In an embodiment of the invention, the one or more cannabinoid lipid carriers comprise one or more flavonoids.

In an embodiment of the invention, the master granule component is a premixture of the one or more solid particles and the one or more cannabinoids reversibly adsorbed onto the one or more solid particles, the one or more cannabinoids applied by means of spraying.

In an embodiment of the invention, the master granule component is a premixture of the one or more solid particles and the one or more cannabinoids reversibly adsorbed onto the one or more solid particles, the one or more cannabinoids applied by means of a thin layer to the surface of the one or more solid particles.

In an embodiment of the invention, the weight ratio of the one or more cannabinoids relative to the one or more solid particles is from 1:30 to 1:1.

In an embodiment of the invention, the weight ratio of the one or more cannabinoids relative to the one or more solid particles is from 1:25 to 1:5.

In an embodiment of the invention, the weight ratio of the one or more cannabinoids relative to the one or more solid particles is from 1:20 to 1:10.

In an embodiment of the invention, the master granule is present in an amount of 5 to 50% by weight of the composition.

In an embodiment of the invention, the master granule is present in an amount of 7 to 30% by weight of the composition.

In an embodiment of the invention, the master granule is present in an amount of 10 to 25% by weight of the composition.

In an embodiment of the invention, the master granule has a volume weighted mean diameter of 10-400 μm.

In an embodiment of the invention, the master granule has a volume weighted mean diameter of 50-300 μm.

In an embodiment of the invention, the master granule component comprises a plurality of solid particles.

In an embodiment of the invention, the plurality of solid particles are present in an amount of at least 5% by weight of the composition.

In an embodiment of the invention, the plurality of solid particles are present in an amount of at least 10% by weight of the composition.

In an embodiment of the invention, the plurality of solid particles are present in an amount of at least 20% by weight of the composition.

In an embodiment of the invention, the plurality of solid particles are present in an amount of at most 30% by weight of the composition.

In an embodiment of the invention, the one or more solid particles are water-insoluble.

In an embodiment of the invention, the plurality of solid particles are selected from the group consisting of silica, microcrystalline cellulose, cellulose, silicified microcrystalline cellulose, clay, talc, starch, pregelatinized starch, calcium carbonate, dicalcium phosphate, magnesium carbonate, magnesium-alumino-metasilicates, hyper porous silica and mixtures thereof. In some embodiments of the invention, silica is less preferred in the master granule component. In some embodiments of the invention, silica is to be avoided in the master granule component.

In an embodiment of the invention, the plurality of solid particles comprise microcrystalline cellulose.

In an embodiment of the invention, the one or more solid particles are water-soluble.

In an embodiment of the invention, the plurality of solid particles comprise one or more sugar alcohols. In an embodiment of the invention, the solid particles comprise directly compressible (DC) sugar alcohols. In an embodiment of the invention, the solid particles comprise non-directly compressible (non-DC) sugar alcohols.

In an embodiment of the invention, the one or more solid particles are selected from the group consisting of xylitol, lactitol, sorbitol, maltitol, erythritol, isomalt and mannitol, and mixtures and combinations thereof.

In an embodiment of the invention, the extragranular component does not comprise cannabinoids.

In an embodiment of the invention, the one or more extragranular sugar alcohols are in free form. In this embodiment, the one or more cannabinoids are not associated with the extragranular sugar alcohols.

In an embodiment of the invention, the one or more extragranular sugar alcohols are not associated with the one or more cannabinoids.

In an embodiment of the invention, the content of sugar alcohol in the master granule component is from 5 to 40% by weight of the composition and the content of sugar alcohol in the extracellular component is from 60 to 95% by weight of the of the composition.

In some embodiments of the invention, the content of sugar alcohol in the master granule component is from 10 to 30% by weight of the composition and the content of sugar alcohol in the extracellular component is from 70 to 90% by weight of the composition. In some embodiments of the invention, the content of sugar alcohol in the master granule component is from 20 to 40% by weight of the composition and the content of sugar alcohol in the extracellular component is from 60 to 80% by weight of the composition. In some embodiments of the invention, the content of sugar alcohol in the master granule component is from 5 to 30% by weight of the composition and the content of sugar alcohol in the extracellular component is from 70 to 95% by weight of the composition.

In some embodiments of the invention, the content of sugar alcohol in the composition is more than 80% by weight of the composition, such as more than 90% by weight of the composition. In some embodiments of the invention, the content of sugar alcohol in the composition is more than 85% by weight of the composition. In some embodiments of the invention, the content of sugar alcohol in the composition is more than 90% by weight of the composition. In some embodiments of the invention, the content of sugar alcohol in the composition is more than 95% by weight of the composition.

In some embodiments of the invention, the one or more extragranular sugar alcohols comprise sorbitol, erythritol, xylitol, lactitol, maltitol, mannitol, isomalt, and mixtures and combinations thereof. In some embodiments of the invention, the one or more extragranular sugar alcohols is sorbitol. In some embodiments of the invention, the one or more extragranular sugar alcohols is xylitol. In some embodiments of the invention, the one or more extragranular sugar alcohols is maltitol. In some embodiments of the invention, the one or more extragranular sugar alcohols is erythritol. In some embodiments of the invention, the one or more extragranular sugar alcohols is mannitol. In some embodiments of the invention, the one or more extragranular sugar alcohols is isomalt. In some embodiments of the invention, the one or more extragranular sugar alcohols is not lactitol. In some embodiments of the invention, the one or more extragranular sugar alcohols is not mannitol.

In some embodiments of the invention, the content of microcrystalline cellulose in the master granule component is from 2 to 40% by weight of the composition and the content of sugar alcohol in the extracellular component is from 60 to 98% by weight of the of the composition.

In some embodiments of the invention, the content of microcrystalline cellulose in the master granule component is from 2 to 20% by weight of the composition and the content of sugar alcohol in the extracellular component is from 80 to 98% by weight of the of the composition.

In some embodiments of the invention, the composition is compressed into a lozenge tablet.

In some embodiments of the invention, the composition is compressed at a pressure of more than 5 kN.

In some embodiments of the invention, the composition is compressed at a pressure of more than 15 kN.

In some embodiments of the invention, the composition is compressed at a pressure of more than 30 kN.

In some embodiments of the invention, the composition is compressed at a pressure of 5 to 60 kN.

In some embodiments of the invention, the extragranular component enhances the compressibility of the composition.

In some embodiments of the invention, the master granule component reduces the compressibility of the composition.

In some embodiments of the invention, the master granule component is fragile and reduces the compressibility of the lozenge composition.

In some embodiments of the invention, the extragranular component is present in an amount sufficient to counteract the fragile properties of the master granule component.

In some embodiments of the invention, the composition is disintegrated in contact with saliva after about 5 minutes. In the present context "disintegrated" or "disintegrate" is intended to mean that the lozenge is no longer to be considered a tablet but the tablet has been reduced and dispersed in saliva.

In some embodiments of the invention, the composition is disintegrated in contact with saliva after about 10 minutes.

In some embodiments of the invention, the composition is disintegrated in contact with saliva between 5 and 20 minutes.

In some embodiments of the invention, the composition has a dissolution profile, which provides greater than 90% release of the one or more cannabinoids within 10 to 15 minutes. In the present context "dissolution profile" is intended to mean as measured according to the examples of the invention and 90% release is to occur somewhere in the interval after 10 to 15 minutes.

In some embodiments of the invention, the composition has a dissolution profile, which provides greater than 90% release of the one or more cannabinoids within 15 to 20 minutes.

Importantly, the improved sensorics characteristics of the lozenge formulation of the invention also accommodates an improved release rate of cannabinoids. The reason may be attributed to the fact that if the initial impression by the user is improved and the lozenge texture is also improved, this would trigger the user to effectively use the product. Also, the production of saliva may be enhanced once the product formulation is improved, which in turn may accommodate further increased release of cannabinoids. However, the precise mechanism is not well understood.

In some embodiments of the invention, the composition in contact with saliva has a disintegration profile that varies less than 10% under a compression pressure of 10 to 30 kN. In the present context "disintegration profile" is intended to mean that the weight percent total loss of material from the lozenge for a given time during use varies less than 10% under a tableting force from 10 to 30 kN. The measurement is generally measured while the lozenge is not completely "disintegrated". The measurement is taken while the lozenge is in contact with saliva as an in vivo measurement according to the measurement outlined in the examples of the invention.

In some embodiments of the invention, the composition in contact with saliva has a disintegration profile that varies less than 5% under a compression pressure of 10 to 30 kN.

In some embodiments of the invention, the composition in contact with saliva has a disintegration profile that is substantially the same under a compression pressure of 10 to 30 kN.

One of the observations with great impact of the present invention is that the compression force generally does not have a high influence on the disintegration of the lozenges and even not on the dissolution of the lozenges. Common understanding in the art of tableting is that the compression force has a huge influence on the disintegration and dissolution of tablets. The inventors have discovered that the present formulation of cannabinoids is very advantageous in this aspect. Without being bound by theory, it is believed that the presence of a master granule component in combination with the extragranular components contributes to this behavior of the lozenge.

In some embodiments of the invention, the lozenge composition further comprises a binder, such as a dry or wet binder.

In some embodiments of the invention, the lozenge composition further comprises at least one dissolution modifier selected from the group consisting of acacia, agar, alginic acid or a salt thereof, carbomer, carboxymethylcellulose, carrageenan, cellulose, chitosan, copovidone, cyclodextrins, ethylcellulose, gelatin, guar gum, hydroxyethyl cellulose, hydroxyethyl methylcellulose, hydroxypropyl cellulose, hypromellose, inulin, methylcellulose, pectin, polycarbophil or a salt thereof, polyethylene glycol, polyethylene oxide, polyvinyl alcohol, pullulan, starch, tragacanth, trehalose, xanthan gum and mixtures thereof.

In some embodiments of the invention, the at least one dissolution modifier is selected from the group consisting of alginic acid or a salt thereof, polycarbophil or a salt thereof, xanthan gum and mixtures thereof.

In some embodiments of the invention, the at least one dissolution modifier is selected from the group consisting of sodium alginate, calcium polycarbophil, xanthan gum and mixtures thereof.

In some embodiments of the invention, the at least one dissolution modifier is xanthan gum.

In some embodiments of the invention, the at least one dissolution modifier is located in the master granule component.

In some embodiments of the invention, the lozenge composition further comprises at least one viscolising agent that when hydrated forms a gel having positive surface electrical charge and at least one viscolising agent that when hydrated forms a gel having negative surface electrical charge.

In some embodiments of the invention, the lozenge further comprises at least one alkaline buffering agent selected from the group consisting of sodium carbonate, sodium bicarbonate, potassium phosphate, potassium carbonate and potassium bicarbonate, and mixtures thereof.

In some embodiments of the invention, the at least one alkaline buffering agent is located in the extragranular component.

In some embodiments of the invention, the total amount of the at least one alkaline buffering agent is from about 5 mg to about 20 mg.

In some embodiments of the invention, the lozenge composition further comprises at least one optional excipient selected from the group consisting of high intensity sweeteners, flavors, chelating agents, glidants or colorants.

In some embodiments of the invention, the unit weight of the lozenge composition is from about 200 mg to about 2000 mg.

In some embodiments of the invention, the one or more cannabinoids are present in an amount of 0.1 to 400 mg.

In some embodiments of the invention, the one or more cannabinoids are present in an amount of 10 to 100 mg.

In an embodiment of the invention, the one or more cannabinoids are present in an amount of 0.1 to 200 mg. In some other embodiments of the invention, the one or more cannabinoids are present in an amount of 0.1 to 100 mg. In some other embodiments of the invention, the one or more cannabinoids are present in an amount of 0.1 to 50 mg. In an embodiment of the invention said lozenge comprises said cannabinoids in an amount of 0.1-30 mg, such as 1-20 mg, such as 5-15 mg.

In some embodiments of the invention, the one or more cannabinoids comprise cannabidiol (CBD), cannabidiolic acid (CBDA), cannabidivarin (CBDV), salts and derivatives thereof.

In some embodiments of the invention, the one or more cannabinoids comprise tetrahydrocannabinol (THC), tetrahydrocannabinolic acid (THCA), tetrahydrocannabivarin (THCV), salts and derivatives thereof.

In some embodiments of the invention, the one or more cannabinoids comprise cannabigerol (CBG), salts and derivatives thereof.

In some embodiments of the invention, the cannabinoid is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabinol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), salts thereof, derivatives thereof and mixtures of cannabinoids.

In an embodiment of the invention, the one or more cannabinoids comprise cannabidiol (CBD), cannabidiolic acid (CBDA), cannabidivarin (CBDV), salts and derivatives thereof. In an embodiment of the invention the one or more cannabinoids comprises CBD, salts and derivatives thereof, including analogues and homologues. In an embodiment of the invention said one or more cannabinoids comprises CBD. In an embodiment of the invention said one or more cannabinoids is CBD.

In an embodiment of the invention, the one or more cannabinoids comprise tetrahydrocannabinol (THC), tetrahydrocannabinolic acid (THCA), tetrahydrocannabivarin (THCV), salts and derivatives thereof. In an embodiment of the invention said one or more cannabinoids comprises tetrahydrocannabinol (THC). Preferably THC is intended to mean (−)-trans-Δ⁹-tetrahydrocannabinol, i.e. (6aR,10aR)-delta-9-tetrahydrocannabinol). In an embodiment of the invention said one or more cannabinoids is THC.

In an embodiment of the invention, the one or more cannabinoids comprise at least two cannabinoids. In an embodiment of the invention said one or more cannabinoids comprises a combination of several cannabinoids, such as THC and CBD. In an embodiment of the invention said one or more cannabinoids is a combination of THC and CBD.

In an embodiment of the invention, the lozenge formulation comprises flavor in an amount between 0.01 and 10% by weight of the lozenge formulation such as in an amount between 0.01 and 5% by weight of the lozenge formulation.

In an embodiment of the invention, the lozenge formulation comprises high intensity sweetener.

In an embodiment of the invention, the one or more cannabinoids are present in solid form. In an embodiment of the invention, the one or more cannabinoids are present in liquid or semi-liquid form.

In an embodiment of the invention, the one or more cannabinoids form part of a complex with cyclodextrin. This complex may enhance the release of cannabinoids according to the present invention. Also, the complex may enhance delivery of the one or more cannabinoids to the oral mucosa.

In an embodiment of the invention, the one or more cannabinoids comprise at least one phytocannabinoid that forms part of an extract. In some embodiments of the invention, it was seen that cannabinoids as part of an extract may enhance the release of cannabinoids.

In an embodiment of the invention, the one or more cannabinoids comprise at least one isolated cannabinoid.

In an embodiment of the invention, the one or more cannabinoids are located in a protein carrier, such as pea protein carrier.

In an embodiment of the invention, the one or more cannabinoids comprise at least one endocannabinoid or endocannabinoid-like compound, such as palmitoylethanolamide (PEA).

In an embodiment of the invention, the one or more cannabinoids comprise at least one water-soluble cannabinoid. Water-soluble cannabinoids may enhance the release according to the present invention.

In an embodiment of the invention, the one or more cannabinoids are derived from plant material.

In an embodiment of the invention, the composition does not comprise plant material.

In an embodiment of the invention, the composition comprises one or more emulsifiers.

In an embodiment of the invention, the lozenge comprises emulsifiers in an amount of 0.1% to 25% by weight of said lozenge, such as 1-10% by weight of said lozenge, such as 2-8% by weight of said lozenge.

In an embodiment of the invention, the emulsifiers are selected from the group of acetylated monoglycerides, mono- and/or di-glycerides of fatty acids such as glycerol monostearate, acetem, lecithin and any combination thereof.

In an embodiment of the invention, the emulsifier has an HLB-value of more than 6, preferably of 8-18.

In an embodiment of the invention, the composition comprises one or more solubilizers.

In an embodiment of the invention, the composition comprises a self-emulsifying agent.

In an embodiment of the invention, the composition comprises a polymer carrier for the one or more cannabinoids.

In an embodiment of the invention, the composition comprises a lipophilic association between the one or more cannabinoids and a fatty acid, such as oleic acid.

In an embodiment of the invention, the composition comprises a lipid carrier for the one or more cannabinoids.

In an embodiment of the invention, the composition comprises enzyme inhibitors or efflux inhibitors.

In an embodiment of the invention, the composition comprises one or more antioxidants.

In an embodiment of the invention, the one or more cannabinoids have a systemic effect.

In an embodiment of the invention, the one or more cannabinoids have a local effect.

In another aspect of the invention, there is provided an intermediate lozenge product for oral administration of cannabinoids, the product comprising the lozenge composition according to the embodiments as described in the embodiments of the invention.

In another aspect of the invention, the lozenge composition may be used for the treatment or alleviation of a medical condition.

In certain embodiments of the invention, the lozenge formulation of the present invention may be used for the treatment or alleviation of a medical condition selected from the group consisting of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In another aspect of the invention, a package is provided comprising a lozenge composition according to the invention, the package comprising a material acting as a barrier for the one or more cannabinoids and oxygen, preferably a copolymer of acrylonitrile and methyl acrylate.

In certain embodiments of the invention, the package includes a liquid or a semisolid for the provision of a preventive environment therein.

In certain embodiments of the invention, the package is a blister package.

DETAILED DESCRIPTION OF THE INVENTION

The invention will now be described in more details with respect to certain aspects and embodiments of the invention. These aspects and embodiments are intended to be understood in connection with the rest of the description, including the Summary of the Invention and the Examples of the invention.

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in connection with the word comprising or containing denote "one or more." The expression "one or more" is intended to mean one, two, three or more.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

The term "particle size" relates to the ability of the particles to move through or be retained by sieve holes of a specific size. As used herein, the term "particle size" refers to the average particle size as determined according to European Pharmacopoeia 9.1 when using test method 2.9.38 particle size distribution estimation by analytical sieving, unless otherwise specifically is mentioned.

The term "plurality of particles" is intended to cover the "population of particles" in the sense that the sum of populations are covered by the term "plurality".

The term "portion of particles" or similar wording is intended to mean a plurality of particles that collectively may comprise one or more populations of particles.

The term "particle" or similar wording is intended to denote a single, discrete composition of solid matter, such as a granule or individual elements in powder, having a certain size that may deviate considerable.

The term "DC sugar alcohol particles" or similar wording refers to particles of direct compressible (DC) sugar alcohol. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC). Also, granulation of non-DC sugar alcohol with water as binder is considered to result in "DC sugar alcohol particles" in the present context. This is contrary to the term "non-DC sugar alcohol particles" that refers to particles of non-directly compressible (non-DC) sugar alcohol. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol.

The term "tableted" or "tablet" or "compressed" is intended to mean that the lozenge composition is pressed in a tableting apparatus and mainly being composed of particulate matter. Although the terms imply a method step, in the present context, the terms are intended to mean the resulting tablet obtained in tableting a portion of particles. It is noted that a tablet or tableted composition that is mentioned to comprise particles eventually is to be understood as particles that have been pressed together in a tableting step.

The term "lozenge" is intended to cover that a "lozenge composition" has been "compressed" into a "lozenge tablet". In the present context, a "lozenge" is intended to mean that the tablet during use in the oral cavity is intended to be sucked or licked on. The term "lozenge" is given the ordinary meaning in the art of lozenges. The intention is not that the lozenge may be chewed. The lozenge does not comprise a gum base. Generally, the "lozenge" of the present invention may disintegrate upon sucking or licked in minutes, contrary to seconds for orally disintegrating tablets (ODT) or fast disintegrating tablets (FDT) tablets. Hence, the intention is that the "lozenge tablet" is to deliver the one or more cannabinoids over time and not immediately. However, the term "intermediate product" refers to products made by the "lozenge formulation" according to the invention that may disintegrate within seconds, such as ODT or FDT tablets.

The term "weight of the lozenge composition" or similar wording meaning the same is defined in the present context as weight of the lozenge composition, not including the weight of an outer coating, such as a hard coating, soft coating, and the like.

By the phrase "texture" is meant a qualitative measure of the properties of the lozenge composition or lozenge and of the overall mouth-feel experienced by the user during use. Thus, the term "texture" encompasses measurable quantities such as hardness as well as more subjective parameters related to the feel experienced by a user.

The term "in vivo use" intends to mean that the lozenge composition system is used by a human subject in an experimental setup of trained test persons according to statistically principles and that either the saliva of the human subject is subject to measurements or the lozenge composition is subject to measurements.

The term "in vivo release" or "in vivo testing of release" or similar wording intends to mean that the lozenge composition is tested as outlined in the examples.

The term "in vitro release" or "in vitro testing of release" or similar wording intends to mean that the lozenge composition is tested according to the examples.

The term "release" in the present context is intended to mean under "in vitro" conditions if not stated otherwise. In particular, the "release rate" during a certain period of time is intended to mean the amount in percentage of cannabinoids that is released during the period.

The term "sustained release" or "extended release" is herein intended to mean prolonged release over time. The term "rapid release" or "quick release" or "high release" is herein intended to mean a higher content released for a given period of time. The term "controlled release" is intended to mean a release of a substance from a lozenge composition by the aid of active use of the lozenge composition in the oral cavity of the subject, whereby the active use is controlling the amount of substance released.

The term "delivery to the oral mucosa" or similar wording intends to mean that the lozenge composition is tested according to the examples.

In one embodiment of the invention, the one or more cannabinoids is delivered to mucosal surfaces in the oral cavity.

In one embodiment of the invention, the one or more cannabinoids is delivered to mucosal surfaces in the gastrointestinal tract.

In one embodiment of the invention, the one or more cannabinoids is delivered to mucosal surfaces both in the oral cavity and the gastrointestinal tract.

A "self-emulsifying agent" is an agent which will form an emulsion when presented with an alternate phase with a minimum energy requirement. In contrast, an emulsifying agent, as opposed to a self-emulsifying agent, is one requiring additional energy to form an emulsion.

In an embodiment of the invention, the lozenge composition comprises further lozenge composition ingredients selected from the group consisting of flavors, dry-binders, tableting aids, anti-caking agents, emulsifiers, antioxidants, enhancers, mucoadhesives, absorption enhancers, high intensity sweeteners, softeners, colors, active ingredients, water-soluble indigestible polysaccharides, water-insoluble polysaccharides or any combination thereof.

According to embodiments of the invention, the emulsifiers may be selected from the group consisting of sucrose ester of fatty acids (such as sucrose mono stearate), polyethylene glycol esters or ethers (PEG) (such as caprylocaproyl macrogol-8 glycerides and lauroyl macrogol-32- glycerides), mono- and diglyceride of fatty acids (such as glycerol monostearate, glycerol monolaurate, glyceryl behenate ester), acetic acid esters of mono- and diglycerides of fatty acids (Acetem), polyoxyethylene alkyl ethers, diacetyl tartaric ester of monoglycerides, lactylated mono-glycerides, glycerophospholipids (such as lecithin), polox-amer (non-ionic block copolymer of ethylene oxide and propylene oxide), cyclodextrins, fatty acid esters of sorbitol (such as sorbitan monolaurate, sorbitan monostearate, sor-bitan tristearate, polysorbates). Self-emulsifying emulsifiers may be phospholipids (Lecithin), Polysorbates (polysorbate 80).

SEDDS (self-emulsifying drug delivery system) may con-sist of hard or soft capsules filled with a liquid or a gel that consists of self-emulsifiers, one or more cannabinoids, oil (to dissolve the cannabinoids) and a surfactant. SEDDS may comprise of a blend or mixture of self-emulsifiers, one or more cannabinoids, oil (to dissolve the cannabinoids) and a surfactant. SEDDS may comprise granules comprising self-emulsifiers, one or more cannabinoids, oil (to dissolve the cannabinoids), one or more surfactants, solvent and co-solvents. Upon contact with gastric fluid, the SEDDS spon-taneously emulsify due to the presence of surfactants. Many surfactants, however, are lipid based and interact with lipases in the GIT (gastro intestinal tract). This can lead to a reduced capability of the lipid-based surfactants to emul-sify the one or more cannabinoids as well as the oil carrier, both reducing bioavailability.

In the present context, SEDDS is a solid or liquid dosage form comprising an oil phase, a surfactant and optionally a co-surfactant, characterized primarily in that said dosage form can form oil-in-water emulsion spontaneously in the oral cavity or at ambient temperature (referring generally to body temperature, namely 37° C.) with mild stirring. When a SEDDS enters the oral cavity, it is initially self-emulsified as emulsion droplets and rapidly dispersed throughout the oral cavity, and thus reducing the irritation caused by the direct contact of the drug with the mucous membrane of the oral cavity. In the oral cavity, the structure of the emulsion microparticulate will be changed or destroyed. The resulting microparticulate of micrometer or nanometer level can pen-etrate into the mucous membrane of the oral cavity, and the digested oil droplets enter the blood circulation, thereby significantly improving the bioavailability of the drug.

Particularly with respect to SEDDS, the formulation of the present invention may provide some clear benefits, both allowing a higher load of cannabinoids and at the same time offer improved sensorics properties of the formulation dur-ing use. Other advantages are also present. Compared to prior art formulations, it is believed that the combination of the component where the one or more cannabinoids are associated and the extragranular component partly provides the benefits of the present invention both with respect to loading of cannabinoids and improved sensorics properties, such as less off-notes.

In an embodiment of the invention, the one or more self-emulsifiers are selected from the group consisting of PEG-35 castor oil, PEG-6 oleoyl glycerides, PEG-6 lino-leoyl glycerides, PEG-8 caprylic/capric glyceride, sorbitan monolaurate, sorbitan monooleate, polyoxyethylene (20) sorbitan monolaurate, polyoxyethylene (60) sorbitan monostearate, polyoxyethylene (80) sorbitan monooleate, lauroylpoloxyl-32 glycerides, stearoyl polyoxyl-32 glycer-ides, polyoxyl-32 stearate, propylene glycol mono laurate, propylene glycol di laurate, and mixtures and combinations thereof.

According to embodiments of the invention, flavors may be selected from the group consisting of coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits mentioned above.

Petroleum waxes aid in the curing of the finished lozenge composition made from the lozenge composition as well as improve shelf life and texture. Wax crystal size influences the release of flavor. Those waxes high in iso-alkanes have a smaller crystal size than those waxes high in normal-alkanes, especially those with normal-alkanes of carbon numbers less than 30. The smaller crystal size allows slower release of flavor since there is more hindrance of the flavors escape from this wax versus a wax having larger crystal sizes.

Petroleum wax (refined paraffin and microcrystalline wax) and paraffin wax are composed of mainly straight-chained normal-alkanes and branched iso-alkanes. The ratio of normal-alkanes to iso-alkanes varies.

Antioxidants prolong shelf life and storage of lozenge composition, finished lozenge composition or their respec-tive components including fats and flavor oils.

Antioxidants suitable for use in lozenge composition include butylated hydroxyanisole (BHA), butylated hydroxytoluene (BHT), betacarotenes, tocopherols, acidu-lants such as Vitamin C (ascorbic acid or corresponding salts (ascorbates)), propyl gallate, catechins, other synthetic and natural types or mixtures thereof.

Further lozenge composition ingredients, which may be included in the lozenge composition according to the present invention, include surfactants and/or solubilizers. As examples of types of surfactants to be used as solubilizers in a lozenge composition according to the invention, reference is made to H. P. Fiedler, Lexikon der Hilfstoffe für Phar-macie, Kosmetik and Angrenzende Gebiete, pages 63-64 (1981) and the lists of approved food emulsifiers of the individual countries. Anionic, cationic, amphoteric or non-ionic solubilizers can be used. Suitable solubilizers include lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllatylate, sodium lauryl sulfate and sorbitan esters of fatty acids and polyoxyethylated hydrogenated castor oil (e.g. the product sold under the trade name CREMOPHOR), block copolymers of ethylene oxide and propylene oxide (e.g. products sold under trade names PLURONIC and POLOXAMER), polyoxyethylene fatty alcohol ethers, polyoxyethylene sorbitan fatty acid esters, sorbitan esters of fatty acids and polyoxyethylene steraric acid esters.

Particularly suitable solubilizers are polyoxyethylene stearates, such as for instance polyoxyethylene(8)stearate and polyoxyethylene(40)stearate, the polyoxyethylene sor-bitan fatty acid esters sold under the trade name TWEEN, for instance TWEEN 20 (monolaurate), TWEEN 80 (mo-nooleate), TWEEN 40 (monopalmitate), TWEEN 60 (monostearate) or TWEEN 65 (tristearate), mono and diacetyl tartaric acid esters of mono and diglycerides of edible fatty acids, citric acid esters of mono and diglycerides of edible fatty acids, sodium stearoyllatylate, sodium laurylsulfate, polyoxyethylated hydrogenated castor oil, blockcopolymers of ethylene oxide and propyleneoxide and polyoxyethylene fatty alcohol ether. The solubilizer may either be a single compound or a combination of several compounds. In the presence of an active ingredient, such as the included one or more cannabinoids, the lozenge composition may preferably also comprise a carrier known in the arts of lozenge composition and active ingredients. Poloxamer F68 is a further highly suitable solubilizer.

High intensity artificial sweetening agents can also be used according to preferred embodiments of the invention. Preferred high intensity sweeteners include, but are not limited to sucralose, aspartame, salts of acesulfame, alitame, neotame, saccharin and its salts, cyclamic acid and its salts, glycyrrhizin, dihydrochalcones, thaumatin, monellin, monk fruit extract, advantame, stevioside and the like, alone or in combination.

In order to provide longer lasting sweetness and flavor perception, it may be desirable to encapsulate or otherwise control the release of at least a portion of the artificial sweeteners.

Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another lozenge composition component such as a resinous compound.

Usage level of the high-intensity sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated high-intensity sweetener will be proportionately higher.

A lozenge composition and/or lozenge composition may, if desired, include one or more fillers/texturizers including as examples, magnesium- and calcium carbonate, sodium sulphate, ground limestone, silicate compounds such as magnesium- and aluminum silicate, kaolin and clay, aluminum oxide, silicium oxide, talc, titanium oxide, mono-, diand tri-calcium phosphates, cellulose polymers, such as wood, and combinations thereof. According to an embodiment of the invention, one preferred filler/texturizer is calcium carbonate.

A number of lozenge composition components well known within the art may be applied within the scope of the present invention. Such components comprise but are not limited to waxes, fats, softeners, fillers, bulk sweeteners, flavors, antioxidants, emulsifiers, coloring agents, binding agents and acidulants.

In an embodiment of the invention, water-soluble ingredients comprise at least one sugar alcohol. The at least one sugar alcohol may be selected from the group consisting of xylitol, sorbitol, mannitol, maltitol, isomaltitol, isomalt, erythritol, lactitol, maltodextrin, hydrogenated starch hydrolysates, and combinations thereof.

In an aspect of the invention, the sugar alcohol of the invention may be replaced by one or more sugars, such as a sugar selected from the group consisting of dextrose, sucrose, maltose, fructose, lactose, and combinations thereof.

The lozenge according to the invention is manufactured by applying pressure to a content of particles by suitable compression means. The particles or powder is then pressed into a compact coherent tablet. The particles may for example comprise so-called primary particles or aggregated primary particles. When these are pressed, bonds are established between the particles or granules, thereby conferring a certain mechanical strength to the pressed tablet.

It should be noted that the above-introduced terms: powder, primary particles and aggregated primary particles may be somewhat misleading in the sense that the difference between primary particles and aggregated primary particles may very often be looked upon differently depending on the background of the user. Some may for instance regard a sweetener, such as sorbitol, as a primary particle in spite of the fact that sorbitol due to the typically preprocessing performed on sorbitol when delivered to the customer should rather be regarded as some sort of aggregated primary particles. The definition adopted in the description of this invention is that aggregated primary particles refer to macro-particles comprising more or less preprocessed primary particles.

When pressure is applied to the particles, the bulk volume is reduced, and the amount of air is decreased. During this process energy is consumed. As the particles come into closer proximity to each other during the volume reduction process, bonds may be established between the particles or granules. The formation of bonds is associated with a reduction in the energy of the system as energy is released. Volume reduction takes place by various mechanisms and different types of bonds may be established between the particles or granules depending on the pressure applied and the properties of the particles or granules. The first thing that happens when a powder is pressed is that the particles are rearranged under low compaction pressures to form a closer packing structure. Particles with a regular shape appear to undergo rearrangement more easily than those of irregular shape. As the pressure increases, further rearrangement is prevented, and subsequent volume reduction is obtained by plastic and elastic deformation and/or fragmentation of the tablet particles. Brittle particles are likely to undergo fragmentation, i.e. breakage of the original particles into smaller units. Plastic deformation is an irreversible process resulting in a permanent change of particle shape, whereas the particles resume their original shape after elastic deformation. Evidently, both plastic and elastic deformation may occur, when compressing a lozenge composition.

By the method of the invention, it is possible to form one-layered or multi-layered tablets, such as two-layered tablets or three-layered tablets.

Several studies of the bond types in pressed tablets have been made over the years, typically in the context of pharmaceuticals and several techniques of obtaining pressed tablets on the basis of available powders has been provided. Such studies have been quite focused on what happens when the volume reduction is performed and how the end-product may be optimized for the given purpose. Several refinements with respect to pressed tablets has for instance been made in the addition of for example binders in the tablet raw materials for the purpose of obtaining a sufficient strength to the final pressed tablet while maintaining acceptable properties, e.g. with respect to release.

In accordance with the invention, the tableted lozenge composition according to the invention may comprise about 0.1 to about 75% by weight of an outer coating applied onto the lozenge composition centre. Thus, suitable coating types include hard coatings, film coatings and soft coatings of any composition including those currently used in coating of tableted lozenge composition.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the lozenge composition centres for various reasons. In a typical process of providing the lozenge composition centres with a protective sugar coating, the lozenge composition centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or active compounds.

In a typical hard coating process as it will be described in detail in the following, a suspension containing crystallisable sugar and/or polyol is applied onto the lozenge composition centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished lozenge composition element, such as about 10 to about 60% by weight, including about 15 to about 50% by weight.

In further useful embodiments, the outer coating of the lozenge composition element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a lozenge composition centre of any of the above forms. The thickness of such a coating is usually between 20 and 100 μm.

Generally, the film coating is obtained by passing the lozenge composition centres through a spray zone with atomized droplets of the coating materials in a suitable aqueous or organic solvent vehicle, after which the material adhering to the lozenge composition centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the lozenge composition formulation. Such release modifying polymers include methylacrylate ester copolymers, ethylcellulose (EC) and enteric polymers designed to resist the acidic stomach environment. The latter group of polymers include: cellulose acetate phtalate (CAP), polyvinyl acetate phtalate (PVAP), shellac, metacrylic acid copolymers, cellulose acetate trimellitate (CAT) and HPMC. It will be appreciated that the outer film coating according to the present invention may comprise any combination of the above film-coating polymers.

According to the invention, the one or more cannabinoids may be selected from various cannabinoids.

"Cannabinoids" are a group of compounds including the endocannabinoids, the phytocannabinoids and those which are neither endocannabinoids or phytocannabinoids, hereinafter "syntho-cannabinoids".

"Endocannabinoids" are endogenous cannabinoids, which may have high affinity ligands of CB1 and CB2 receptors.

"Phytocannabinoids" are cannabinoids that originate in nature and can be found in the *Cannabis* plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the *Cannabis* plant. Examples include WIN 55212 and rimonabant.

An "isolated phytocannabinoid" is one which has been extracted from the *Cannabis* plant and purified to such an extent that the additional components such as secondary and minor cannabinoids and the non-cannabinoid fraction have been substantially removed.

A "synthetic cannabinoid" is one which has been produced by chemical synthesis. This term includes modifying an isolated phytocannabinoid, by, for example, forming a pharmaceutically acceptable salt thereof.

A "substantially pure" cannabinoid is defined as a cannabinoid which is present at greater than 95% (w/w) pure. More preferably greater than 96% (w/w) through 97% (w/w) thorough 98% (w/w) to 99% % (w/w) and greater.

A "highly purified" cannabinoid is defined as a cannabinoid that has been extracted from the *Cannabis* plant and purified to the extent that other cannabinoids and non-cannabinoid components that are co-extracted with the cannabinoids have been substantially removed, such that the highly purified cannabinoid is greater than or equal to 95% (w/w) pure.

"Plant material" is defined as a plant or plant part (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

In the context of this application the terms "cannabinoid extract" or "extract of cannabinoids", which are used interchangeably, encompass "Botanical Drug Substances" derived from *Cannabis* plant material. A Botanical Drug Substance is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes:

pulverisation, decoction, expression, aqueous extraction, ethanolic extraction, or other similar processes." A botanical drug substance does not include a highly purified or chemically modified substance derived from natural sources. Thus, in the case of *Cannabis*, "botanical drug substances" derived from *Cannabis* plants do not include highly purified, Pharmacopoeial grade cannabinoids.

The term "*Cannabis* plant(s)" encompasses wild type *Cannabis sativa* and also variants thereof, including *Cannabis* chemovars which naturally contain different amounts of the individual cannabinoids, *Cannabis sativa* subspecies *indica* including the variants var. *indica* and var. *kafiristanica, Cannabis indica, Cannabis ruderalis* and also plants which are the result of genetic crosses, self-crosses or hybrids thereof. The term "*Cannabis* plant material" is to be interpreted accordingly as encompassing plant material derived from one or more *Cannabis* plants. For the avoidance of doubt it is hereby stated that "*Cannabis* plant material" includes dried *Cannabis* biomass.

Preferably the one or more cannabinoids are selected from: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC. This list is not exhaustive and merely details the cannabinoids which are identified in the present application for reference.

So far, more than 120 different phytocannabinoids have been identified which are within the scope of the present invention.

Cannabinoids can be split into different groups as follows: Phytocannabinoids; Endocannabinoids; and Synthetic cannabinoids.

Cannabinoid receptors can be activated by three major groups of agonist ligands, for the purposes of the present invention and whether or not explicitly denominated as such herein, lipophilic in nature and classed respectively as: endocannabinoids (produced endogenously by mammalian cells); phytocannabinoids (such as cannabidiol, produced by the *Cannabis* plant); and, synthetic cannabinoids (such as HU-210).

Phytocannabinoids can be found as either the neutral carboxylic acid form or the decarboxylated form depending on the method used to extract the cannabinoids. For example, it is known that heating the carboxylic acid form will cause most of the carboxylic acid form to decarboxylate.

Phytocannabinoids can also occur as either the pentyl (5 carbon atoms) or propyl (3 carbon atoms) variant. For example, the phytocannabinoid THC is known to be a CB1 receptor agonist whereas the propyl variant THCV has been discovered to be a CB1 receptor antagonist meaning that it has almost opposite effects.

According to the invention, examples of phytocannabinoids may be cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) and tetrahydrocannabivarinic acid (THCV A). More preferably the one or more cannabinoid is CBD or THC.

The formulation according to the present invention may also comprise at least one cannabinoid selected from those disclosed in A. Douglas Kinghorn et al., Phytocannabinoids, Vol. 103, Chapter 1, pages 1-30.

Examples of endocannabinoids are molecules that activate the cannabinoid receptors within the body. Examples include 2-arachidonyl glycerol (2AG), 2-arachidonyl glyceryl ether (2AGE), arachidonyl dopamine, and arachidonyl ethanolamide (anandamide). Structurally related endogenous molecules have been identified that share similar structural features, but that display weak or no activity towards the cannabinoid receptors but are also termed endocannabinoids. Examples of these endocannabinoid lipids include 2-acyl glycerols, alkyl or alkenyl glyceryl ethers, acyl dopamines and N-acylethanolamides that contain alternative fatty acid or alcohol moieties, as well as other fatty acid amides containing different head groups. These include N-acylserines as well as many other N-acylated amino acids. Examples of cannabinoid receptor agonists are neuromodulatory and affect short-term memory, appetite, stress response, anxiety, immune function and analgesia.

In one embodiment the cannabinoid is palmitoylethanolamide (PEA) which is an endogenous fatty acid amide belonging to the class of nuclear factor agonists.

Synthetic cannabinoids encompass a variety of distinct chemical classes: the cannabinoids structurally related to THC, the cannabinoids not related to THC, such as (cannabimimetics) including the aminoalkylindoles, 1,5-diarylpyrazoles, quinolines, and arylsulfonamides, and eicosanoids related to the endocannabinoids. All or any of these cannabinoids can be used in the present invention.

It is preferred that the formulation comprises one or two primary cannabinoids, which are preferably selected from the group consisting of, cannabidiol (CBD) or cannabidivarin (CBDV), tetrahydrocannabinol (THC), tetrahydrocannabivarin (THCV), tetrahydrocannabinolic acid (THCA), cannabigerol (CBG) and cannabidiolic acid (CBDA) or a combination thereof. It is preferred that the formulation comprises cannabidiol and/or tetrahydrocannabinol.

Preferably, the lozenge composition of the present invention may be used for the treatment or alleviation of pain, epilepsy, cancer, nausea, inflammation, congenital disorders, neurological disorders, oral infections, dental pain, sleep apnea, psychiatric disorders, gastrointestinal disorders, inflammatory bowel disease, appetite loss, diabetes and fibromyalgia.

In a further aspect of the present invention the oral cannabinoid formulation is suitable for use in the treatment of conditions requiring the administration of a neuroprotectant or anti-convulsive medication.

The oral cannabinoid formulation may be for use in the treatment of seizures.

The oral cannabinoid formulation may be for use in the treatment of Dravet syndrome, Lennox Gastaut syndrome, myoclonic seizures, juvenile myoclonic epilepsy, refractory epilepsy, schizophrenia, juvenile spasms, West syndrome, infantile spasms, refractory infantile spasms, tuberous sclerosis complex, brain tumours, neuropathic pain, *Cannabis* use disorder, post-traumatic stress disorder, anxiety, early psychosis, Alzheimer's disease, and autism.

The following non-limiting examples illustrate different variations of the present invention. The examples are meant for indicating the inventive concept; hence the mentioned examples should not be understood as exhaustive for the present. In particular, CBD is used as an exemplary compound, but may also be another cannabinoid.

EXAMPLES

Example 1

Component with CBD Extract 50%

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 2

Component with CBD Extract 10%

CBD extract with a 10% content of CBD provided by Medical Hemp (batch number MH131B Gold), was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on top of one or more sugar alcohol particles. After mixing until CBD was homogeneously distributed in the one or more sugar alcohol particles, the mixture was sieved through a 1400 microns sieve.

Example 3

Component with CBD Isolate with a Solvent

CBD isolate from *Cannabis* plant tissues (phytocannabinoid) with a 98.5% content of CBD provided by Medical Hemp (batch number MH18212) was dissolved in a 96% ethanol solution. The ratio between the CBD isolate and ethanol was 1:1. Once CBD was dissolved in ethanol, the CBD isolate was applied in a premix with one or more sugar alcohol particles. After mixing until CBD was homogeneously distributed in the one or more sugar alcohol particles, the mixture was sieved through a 1400 microns sieve.

Example 4

Component with CBD Isolate without a Solvent

CBD isolate from *Cannabis* plant tissues (phytocannabinoid) with a 98.5% content of CBD provided by Medical Hemp (batch number MH18212) was added as free powder and mixed with one or more sugar alcohol particles. After mixing until CBD was homogeneously distributed in the one or more sugar alcohol particles, the mixture was sieved through a 1400 microns sieve.

Example 5

Component Including Microcrystalline Cellulose

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on microcrystalline cellulose (MCC). Mixing was conducted until the CBD was homogeneously distributed in the MCC. Optionally, the CBD-MCC premix could be further mixed with one or more sugar alcohol particles. The mixture was sieved through a 1400 microns sieve.

Example 6

Component Including Silicium Dioxide Carrier

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on silicium dioxide (SiO2). Mixing was conducted until the CBD was homogeneously distributed in the SiO2. Optionally, the CBD-SiO2 premix could be further mixed with one or more sugar alcohol particles. The mixture was sieved through a 1400 microns sieve.

Example 7

Component Including Hyperporous Silica Magnesium-Alumino-Metasilicates

CBD extract with a 50% content of CBD provided by CBDepot (batch number CSFF 2018/5) was preheated to around 60° C. for around 0.5 to 1 hour until the extract was in liquid form. The extract had, beside cannabinoids, a content of fatty acids, glycerol, waxes, terpenes and flavonoids. After the preheating process, the extract was applied as a thin layer on hyperporous silica magnesium-alumino-metasilicates. Mixing was conducted until the CBD was homogeneously distributed in the hyperporous silica magnesium-alumino-metasilicates. Optionally, the CBD-hyperporous silica magnesium-alumino-metasilicates premix could be further mixed with one or more sugar alcohol particles. The mixture was sieved through a 1400 microns sieve.

Example 8

Preparation of Cannabinoid Component with Emulsifier and Oil

Solution of Labrafil M 1944 CS and Maisine CC (1:1) was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 9

Preparation of Cannabinoid Component with Emulsifier, Oil and Co-Solvent

Solution of 60% Labrafac Lipophile WL1349 and 25% Labrasol and 15% Propylene Glycol was mixed. CBD isolate from Example 3 or CBD extract from Example 1 was added and dissolved in the solution to obtain a 33% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 10

Preparation of Cannabinoid Component with Solid Solubilizer

Gelucire 50/13 was melted at app. 60° C. and CBD isolate from Example 3 or CBD extract from Example 1 was added and dissolved in the melted solution to obtain a 50% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 11

Preparation of Cannabinoid Component with Emulsifier and Co-Solvent

CBD extract from Example 1 was preheated at 60° C., until it was in liquid form and then dissolved in Propylene Glycol. Labrasol ALF was then added to obtain a 17% solution of CBD, using a Vortex mixer. The solution with CBD was applied in a premix with one or more sugar alcohols. After mixing until CBD was homogeneously distributed in the one or more sugar alcohols, the mixture was sieved through a 1400 microns sieve.

Example 12

Preparation of Cannabinoid Component with Solubilizer

CBD extract from Example 1 was preheated at 60° C. until it was in liquid form. After the preheating process, the extract was applied in a premix with Soluplus and mixed until the premix was homogeneous, obtaining a 12.5% premix of CBD. The premix was then mixed with one or more sugar alcohols. After mixing until CBD was homogeneously distributed in the one or more sugar alcohols, the mixture was sieved through a 1400 microns sieve.

Example 13

Preparation of Cannabinoid Component with Cyclodextrin and Emulsifier

CBD isolate from Example 3 was added and dissolved in polysorbate 80 to obtain a 10% solution of CBD. The 10% CBD solution was slowly added and mixed into a solution with 4% cyclodextrin to form a CBD-cyclodextrin complex. The water was removed, whereupon the complex was applied in a premix with one or more sugar alcohols. After mixing until the CBD-cyclodextrin complex was homogeneously distributed in the one or more sugar alcohols, the mixture was sieved through a 1400 microns sieve.

Example 14

A: Preparation of Lozenge with One Layer

A cannabinoid component from either one of Examples 1 to 13 and an extragranular component were blended in a mixing container at about 7-9 rpm and optionally loaded with processing aid in order to improve free-flowing properties of the particles and to avoid stickiness.

In a first step, half the extragranular component was added to a mixing container. High-intensity sweetener (HIS), flavors and the cannabinoid component were added to the container, after which the other half of the extragranular component was added. The mixture was tumbled at 7-9 rpm for 10 minutes. A processing aid was added and the mixture was tumbled at 7-9 rpm for another 2 minute. Hereafter, the mixture was ready for tableting.

The mixture was subsequently led to a standard tablet pressing machine (3090i, available from Fette GmbH) comprising dosing apparatus (P 3200 C, available from Fette GmbH, Germany) and pressed into lozenges. The filling depth in the apparatus was 11.0 mm and the diameter 15.0 mm. The tablets were pressed using a pressing pressure of 20 kN, unless stated otherwise, and optionally prepressed with a pressing pressure of 1-7 kN. There were 75 punches on the rotor, and the rotor speed used was 11 rpm. The individual tablets had a weight of approx. 1 g. The content of CBD in the lozenges was 10 mg.

B: Preparation of Lozenge with Two Layers

A layer with the same ingredients, and prepared in the same way, as in Example 14A was tableted on top of the first layer from Example 14A. The ratio of the ingredients were different in this second layer. The weight ratio of the two layers was 70 to 30 (first layer to second layer). The individual tablets had a weight of approx. 1.7 g. The content of CBD in the lozenges was 20 mg.

Example 15

Composition of Cannabinoid Lozenges with Different CBD Source

Cannabinoid lozenges based on the procedure in Example 14A were made with the formulations outlined in the examples below. In all of the lozenge examples, the amount of the various ingredients is given as % by weight of the lozenge.

TABLE 1

| It was secured that CBD was thoroughly mixed into the premixture. | | | | | |
|---|---|---|---|---|---|
| | Lozenge Number | | | | |
| | 100 | 101 | 102 | 103 | 104 |
| Raw material name | Content [%] | Content [%] | Content [%] | Content [%] | Content [%] |
| Pre-mixture component | | | | | |
| Isomalt | 20 | 20 | 20 | 20 | 20 |
| CBD-extract (loaded 50%) | 2 | 2 | | | |
| CBD isolate (loaded 98.5%) - dissolved in ethanol 1:1 | | | 1.015 | 1.015* | 1.015 |

TABLE 1-continued

It was secured that CBD was thoroughly mixed into the premixture.

| | Lozenge Number | | | | |
|---|---|---|---|---|---|
| | 100 | 101 | 102 | 103 | 104 |
| Raw material name | Content [%] | Content [%] | Content [%] | Content [%] | Content [%] |
| (Example 3) Extragranular component | | | | | |
| Isomalt DC | 73.23 | 71.73 | 74.215 | 74.215 | 72.715 |
| Flavor | 4.2 | 4.2 | 4.2 | 4.2 | 4.2 |
| HIS | 0.07 | 0.07 | 0.07 | 0.07 | 0.07 |
| Processing aids | 0.5 | 0.5 | 0.5 | 0.5 | 0.5 |
| Xanthan gum | | 1.5 | | | 1.5 |
| Total | 100 | 100 | 100 | 100 | 100 |

*CBD isolate has been added loosely to the pre-mixture - not dissolved in ethanol - according to the procedure in Example 4 (deviation of the procedure in Example 3).

Example 16

Composition of Cannabinoid Lozenges with Different Ratios of Premixture

Cannabinoid lozenges based on the procedure in Example 14A were made with the formulations outlined in the examples below. In all of the lozenge examples, the amount of the various ingredients is given as % by weight of the lozenge.

TABLE 2

It was secured that CBD was thoroughly mixed into the premixture.

| | Lozenge Number | | | |
|---|---|---|---|---|
| | 105 | 106 | 107 | 108 |
| Raw material name | Content [%] | Content [%] | Content [%] | Content [%] |
| Pre-mixture component | | | | |
| Isomalt | 4.5 | 8 | 18 | 28 |
| CBD-extract (loaded 50%) | 2 | 2 | 2 | 2 |
| Extragranular component | | | | |
| Isomalt DC | 88.73 | 85.23 | 75.23 | 65.23 |
| Flavor | 4.2 | 4.2 | 4.2 | 4.2 |
| HIS | 0.07 | 0.07 | 0.07 | 0.07 |
| Processing aids | 0.5 | 0.5 | 0.5 | 0.5 |
| Total | 100 | 100 | 100 | 100 |

Example 17

Composition of Cannabinoid Lozenges with Different Sugar Alcohol Particles

Cannabinoid lozenges based on the procedure in Example 14A were made with the formulations outlined in the examples below. In all of the lozenge examples, the amount of the various ingredients is given as % by weight of the lozenge.

TABLE 3

It was secured that CBD was thoroughly mixed into the premixture.

| | Lozenge Number | | | | |
|---|---|---|---|---|---|
| | 109 | 110 | 111 | 112 | 113 |
| Raw material name | Content [%] | Content [%] | Content [%] | Content [%] | Content [%] |
| Pre-mixture component | | | | | |
| Isomalt | 20 | | | | |
| Xylitol | | 20 | | | |
| Mannitol | | | 20 | | |
| Maltitol | | | | 20 | |
| Sorbitol | | | | | 20 |
| CBD-extract (loaded 50%) | 2 | 2 | 2 | 2 | 2 |
| Extragranular component | | | | | |
| Isomalt DC | 73.23 | | | | |
| Xylitol DC | | 73.23 | | | |
| Mannitol DC | | | 73.23 | | |
| Maltitol DC | | | | 73.23 | |
| Sorbitol | | | | | 73.23 |
| Flavor | 4.2 | 4.2 | 4.2 | 4.2 | 4.2 |
| HIS | 0.07 | 0.07 | 0.07 | 0.07 | 0.07 |
| Processing aids | 0.5 | 0.5 | 0.5 | 0.5 | 0.5 |
| Total | 100 | 100 | 100 | 100 | 100 |

Example 18

Composition of Cannabinoid Lozenges with Different Sugar Alcohol Particles

Cannabinoid lozenges based on the procedure in Example 14A were made with the formulations outlined in the examples below. In all of the lozenge examples, the amount of the various ingredients is given as % by weight of the lozenge.

TABLE 4

| It was secured that CBD was thoroughly mixed into the premixture. | | | | | | |
|---|---|---|---|---|---|---|
| | Lozenge Number | | | | | |
| Raw material name | 114 Content [%] | 115 Content [%] | 116 Content [%] | 117 Content [%] | 118 Content [%] | 119 Content [%] |
| Pre-mixture component | | | | | | |
| Isomalt | 20 | | | | | |
| Xylitol | | 20 | | | | 20 |
| Mannitol | | | 20 | | | |
| Maltitol | | | | 20 | | |
| Sorbitol | | | | | 20 | |
| CBD isolate (loaded 98.5%) - dissolved in ethanol 1:1 (Example 3) | 1.015 | 1.015 | 1.015 | 1.015 | 1.015 | 1.015 |
| Extragranular component | | | | | | |
| Isomalt DC | 74.215 | | | | | |
| Xylitol DC | | 74.215 | | | | |
| Mannitol DC | | | 74.215 | | | |
| Maltitol DC | | | | 74.215 | | 74.215 |
| Sorbitol | | | | | 74.215 | |
| Flavor | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

Example 19

Composition of Cannabinoid Lozenges with Microcrystalline Cellulose

Cannabinoid lozenges based on the procedure in Example 14A were made with the formulations outlined in the examples below. In all of the lozenge examples, the amount of the various ingredients is given as % by weight of the lozenge.

TABLE 5

| It was secured that CBD was thoroughly mixed into the premixture. | | | | | | |
|---|---|---|---|---|---|---|
| | Lozenge Number | | | | | |
| Raw material name | 120 Content [%] | 121 Content [%] | 122 Content [%] | 123 Content [%] | 124 Content [%] | 125 Content [%] |
| Pre-mixture component | | | | | | |
| Maltitol | 20 | 20 | 20 | 20 | 20 | 20 |
| MCC | | 2 | 4 | 10 | 4 | 4 |
| CBD-extract (loaded 50%) | 2 | 2 | 2 | 2 | | |
| CBD isolate (loaded 98.5%) - dissolved in ethanol 1:1 (Ex 3) | | | | | 1.015* | 1.015 |
| Extragranular component | | | | | | |
| Maltitol DC | 73.23 | 71.23 | 69.23 | 63.23 | 70.215 | 70.215 |
| Flavor | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

*CBD isolate has been added loosely to the pre-mixture - not dissolved in ethanol - according to the procedure in Example 4 (deviation of the procedure in Example 3).

Example 20

Composition of Cannabinoid Lozenges with Silicium Dioxide as a Carrier

Cannabinoid lozenges based on the procedure in Example 14A were made with the formulations outlined in the examples below. In all of the lozenge examples, the amount of the various ingredients is given as % by weight of the lozenge.

TABLE 6

It was secured that CBD was thoroughly mixed into the premixture.

| | Lozenge Number | | | | | |
|---|---|---|---|---|---|---|
| Raw material name | 126 Content [%] | 127 Content [%] | 128 Content [%] | 129 Content [%] | 130 Content [%] | 131 Content [%] |
| Pre-mixture component | | | | | | |
| Maltitol | 20 | 20 | 20 | 20 | 20 | 20 |
| SiO2 | | 2 | 4 | 10 | 4 | 4 |
| CBD-extract (loaded 50%) | 2 | 2 | 2 | 2 | | |
| CBD isolate (loaded 98.5%) - dissolved in ethanol 1:1 (Ex 3) | | | | | 1.015* | 1.015 |
| Extragranular component | | | | | | |
| Maltitol DC | 73.23 | 71.23 | 69.23 | 63.23 | 70.215 | 70.215 |
| Flavor | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

*CBD isolate has been added loosely to the pre-mixture - not dissolved in ethanol - according to the procedure in Example 4 (deviation of the procedure in Example 3).

Example 21

Composition of Cannabinoid Lozenges with Hyperporous Carrier

Cannabinoid lozenges based on the procedure in Example 14A were made with the formulations outlined in the examples below. In all of the lozenge examples, the amount of the various ingredients is given as % by weight of the lozenge.

TABLE 7

It was secured that CBD was thoroughly mixed into the premixture.

| | Lozenge Number | | | | | |
|---|---|---|---|---|---|---|
| Raw material name | 132 Content [%] | 133 Content [%] | 134 Content [%] | 135 Content [%] | 136 Content [%] | 137 Content [%] |
| Pre-mixture component | | | | | | |
| Maltitol | 20 | 20 | 20 | 20 | 20 | 20 |
| Hyperporous carrier** | | 2 | 4 | 10 | 4 | 4 |
| CBD-extract (loaded 50%) | 2 | 2 | 2 | 2 | | |
| CBD isolate (loaded 98.5%) - dissolved in ethanol 1:1 (Ex 3) | | | | | 1.015* | 1.015 |
| Extragranular component | | | | | | |
| Maltitol DC | 73.23 | 71.23 | 69.23 | 63.23 | 70.215 | 70.215 |
| Flavor | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

*CBD isolate has been added loosely to the pre-mixture - not dissolved in ethanol - according to the procedure in Example 4 (deviation of the procedure in Example 3).
Hyperporous carrier** hyperporous silica magnesium-alumino-metasilicates.

Example 22

Composition of Cannabinoid Lozenges with Different Self-Emulsifying Drug Delivery System (SEDDS) Components Cannabinoid lozenges based on the procedure in Example 14A were made with the formulations outlined in the examples below. In all of the lozenge examples, the amount of the various ingredients is given as % by weight of the lozenge.

TABLE 8

It was secured that CBD was thoroughly mixed into the premixture.

| Raw material name | Lozenge Number | | | | | |
| | 138 Content [%] | 139 Content [%] | 140 Content [%] | 141 Content [%] | 142 Content [%] | 143 Content [%] |
| --- | --- | --- | --- | --- | --- | --- |
| Pre-mixture component | | | | | | |
| Maltitol | 27.0 | 27.0 | 27.0 | 30.0 | 30.0 | 30.0 |
| CBD-extract (loaded 50%) | | | | 2.0 | 2.0 | |
| CBD isolate (loaded 98.5%) | 1.0 | 1.0 | 1.0 | | | |
| Labrafil M 1944 CS | 1.0 | | | | | |
| Gelucire 50/13 | | | 1.0 | | | |
| Labrasol ALF | | 0.5 | | 2.0 | | |
| Maisine CC | 2.0 | | | | | |
| Labrafac Lipophile WL 1349 | | 1.2 | | | | |
| Propylene Glycol | | 0.3 | | 2.0 | | |
| Soluplus | | | | | 6.0 | |
| CBD-cyclodextrin | | | | | | 6.0 |
| Extragranular component | | | | | | |
| Maltitol DC | 64.2 | 65.2 | 66.2 | 59.2 | 57.2 | 59.2 |
| Flavors | 4.2 | 4.2 | 4.2 | 4.2 | 4.2 | 4.2 |
| HIS | 0.07 | 0.07 | 0.07 | 0.07 | 0.07 | 0.07 |
| Processing aids | 0.5 | 0.5 | 0.5 | 0.5 | 0.5 | 0.5 |
| Total | 100 | 100 | 100 | 100 | 100 | 100 |

Example 22A

Composition of Cannabinoid Lozenges with Different Active Ingredients, Terpenes and Antioxidants Cannabinoid lozenges based on the procedure in Example 14A were made with the formulations outlined in the examples below. In all of the lozenge examples, the amount of the various ingredients is given as % by weight of the lozenge.

TABLE 8A

It was secured that the active ingredients was homogenous distributed in the final formulation blend.

| Raw material name | Lozenge Number | | | | | |
| | 144 Content [%] | 145 Content [%] | 146 Content [%] | 147 Content [%] | 148 Content [%] | 149 Content [%] |
| --- | --- | --- | --- | --- | --- | --- |
| Pre-mixture component | | | | | | |
| Maltitol | | 20 | 20 | 20 | | 20 |
| *CBD/THC extract (50% CBD/4% THC) | | 2 | | | | 2 |
| *THC extract (loaded 50%) | | | 2 | | | 1 |
| *CBN-extract (loaded 50%) | | | | 2 | | |
| Linalool | | 0.01 | 0.01 | 0.02 | | 0.01 |
| Humulene | | 0.01 | 0.01 | | | 0.01 |
| Myrcene | | 0.01 | | | | 0.01 |
| B-Caryophyllene | | 0.02 | 0.02 | | | 0.02 |
| Extragranular component | | | | | | |
| Maltitol DC | | 73.14 | 73.11 | 73.21 | | 71.65 |
| Flavor | | 4.2 | 4.2 | 4.2 | | 4.2 |

TABLE 8A-continued

It was secured that the active ingredients was homogenous
distributed in the final formulation blend.

| | Lozenge Number | | | | | |
| | 144 Content [%] | 145 Content [%] | 146 Content [%] | 147 Content [%] | 148 Content [%] | 149 Content [%] |
| Raw material name | | | | | | |
|---|---|---|---|---|---|---|
| HIS | | 0.07 | 0.07 | 0.07 | | 0.07 |
| Tocopherol | | 0.02 | 0.04 | | | 0.04 |
| Ascorbic acid | | 0.02 | 0.04 | | | 0.04 |
| Processing aids | | 0.5 | 0.5 | 0.5 | | 0.5 |
| Total | | 100 | 100 | 100 | | 100 |

*Added according to the procedure in Example 1.

Example 23

Composition of Cannabinoid Lozenges with Two Layers

Cannabinoid lozenges based on the procedure in Example 14B were made with the formulations outlined in the examples below. In all of the lozenge examples, the amount of the various ingredients is given as % by weight of each layer of the lozenge.

TABLE 9

It was secured that CBD was thoroughly
mixed into the premixture.

| Raw material name | Content [%] Layer 1 - 1.190 g | Content [%] Layer 2 - 0.510 g |
|---|---|---|
| Pre-mixture component | | |
| Isomalt | 50.00 | 40.00 |
| CBD-extract (loaded 50%) | 2.521 | 1.961 |
| Extragranular component | | |
| Isomalt DC | 41.80 | 52.52 |
| Flavor | 4.2 | 4.2 |
| HIS | 0.07 | 0.07 |
| Processing aids | 1.25 | 1.25 |
| Color | 0.16 | |
| Total | 100 | 100 |

Example 24

In Vivo Testing of Release

A sample lozenge was tested in a test panel of 8 test persons. Test subject abstain from eating and drinking at least 30 minutes before initiation of any test. The test person was a healthy person appointed on an objective basis according to specified requirements. After 0, 3, 5 and 10 minutes, the content of CBD was measured in the remaining lozenge residue. The lozenge was subject to triple measurements for each of the 8 test persons, giving a total of 24 measurements for each sample. An average of the 24 measurements was calculated and the weight % release was calculated based on the original content of CBD in the sample. The content of CBD was measured in the remaining lozenge residue.

The tablet was weighted and placed in the mouth, between the tongue and the palate. The tablet was sucked and turned every 0.5 minute. Once the desired test time was achieved (3, 5 and 10 min.), the tablet was taken out and weighed directly into a measuring glass to be used for analysis of API content. An in vivo dissolution profile was obtained by analyzing the content of the API in the tablet at different dissolution times.

Example 25

In Vitro Testing of Release

A sample lozenge was tested. After 0, 3, 5 and 10 minutes, the content of CBD was measured in the remaining lozenge residue. The lozenge was subject to triple measurements. An average of the measurements was calculated and the weight % release was calculated based on the original content of CBD in the sample. The content of CBD was measured in the remaining lozenge residue.

The lozenge was weighted. Then 25 ml of phosphate buffer was added into a 50 ml measuring tube with screw cap. The lozenge was added to the tube. The tube was fixed horizontally on a shaking table. After shaking, the tablet was analyzed for content of API. An in vitro profile was obtained by analyzing the content of the API in the tablet at different dissolution times.

Example 26

Testing Setup for Measuring CBD Delivered to the Oral Mucosa

A sample was sucked for 5 minutes in a test panel of 8 test persons. Test subject abstain from eating and drinking at least 30 minutes before initiation of any test. The test person was not allowed to swallow during the procedure. The tablet was weighted and placed in the mouth, between the tongue and the palate. The tablet was sucked and turned every 0.5 minute. After one minute, saliva was obtained from the test person and collected in a vessel for later analysis. In tests for 5 minutes release, the same procedure was followed until 5 minutes where the last saliva sample was collected and added to the same vessel for aggregated analysis. The test person was a healthy person appointed on an objective basis according to specified requirements. The aggregated saliva sample was collected after 5 minutes, and the content of CBD was measured in the saliva. The content of CBD was also measured in the remaining residue. The residue, if still present, was positioned in a flask, weighted and analyzed. The residue, if still present, and saliva were subject to 3 triple measurements for each of the 8 test persons, giving a total of 24 measurement for each sample. An average of the 24 measurements was calculated and the weight % release was calculated. By comparing the amount of CBD in the residue and the amount of CBD in the saliva, the amount of CBD delivered to the oral mucosa could be estimated.

Example 27

Sensoric Evaluation Test Set-Up

Apart from dissolution measurements, either in vivo or in vitro, sensoric tests were also performed to reveal very important characteristics and properties of the lozenges. These sensoric parameters are important as indicators of the structure of the lozenge composition. The structure is the underlying guidance as to how the lozenge resembles the structure of a comparative lozenge, which is set as the standard in the test series, i.e. the lozenges are compared to each other in the test series of preferably 5 samples. The test set-up was composed of 8 test persons in a test panel. All of the test persons were healthy individuals appointed on an objective basis according to specified requirements. The sensory analysis was performed according to ISO 4121-2003 in testing conditions following ISO 8589. The result is an average of the results of the 8 individuals.

The test persons gave a rating from "+" to "+++++", where "+" is poor and "+++++" is excellent and comparable to the standard, i.e. "+++++" means that the lozenge was comparable to the standard and "+" means that the lozenge was very far from comparable to the standard. "0" indicated that it was not tested.

Four different parameters were tested in a test panel:

| Friability | Flavor | Sweetness | Off-notes |
|---|---|---|---|

"Texture"—the general impression of the tablet when placed in the mouth with respect to elements such as hardness, roughness and a smoothness.

"Friability"—the impression of the lozenge when placed in the mouth and sucking is commenced. For instance, a very hard and viscous structure gave a very low rating and a very brittle structure also gave a very low rating.

"Flavor"—the overall impression of the lozenge during sucking with respect to flavor. For instance, a very low flavor experience gave a very low rating and a too high flavor experience that was not comparable to the standard also gave a very low rating.

"Sweetness"—the overall impression of the taste of the lozenge during sucking with respect to sweetness. For instance, if the sweetness was decreasing rapidly, a very low rating was given and if the sweetness was too high giving an uncomfortable feeling, a very low rating was also given.

"Off-notes"—the overall impression of the off-note from the one or more cannabinoids in the composition during sucking. For instance, if off-notes (grass, bitter notes, irritation in the throat) were experienced in the throat, a low rating was given and if other uncomfortable sensations was experienced, a low rating was also given.

Example 28

In Vitro Weight Loss

TABLE 10

Lozenge samples were tested for weight loss according to Example 25. The value indicates weight % of cannabinoid released from the lozenge sample.
% weight loss of tablet at in vitro dissolution test

| Sample | 3 min. | 5 min. | 10 min. | 15 min. | 20 min. |
|---|---|---|---|---|---|
| 100 | 39% | 69% | 87% | 100% | |
| 101 | 30% | 53% | 75% | | 100% |
| 102 | 45% | 74% | 87% | 100% | |
| 103 | 39% | 73% | 89% | 100% | |
| 104 | 35% | 57% | 76% | | 100% |

It was very surprising to the inventors that the in vitro dissolution time was 5 minutes longer when xanthan gum was added to the formulation.

Example 29

In Vitro Dissolution Profile

TABLE 11

Lozenge samples were tested for dissolution according to Example 25. The value indicates weight % of cannabinoid released from the lozenge sample.
Dissolution profile - CBD released from the tablet over time

| Sample | 3 min. | 5 min. | 10 min. | 15 min. | 20 min. |
|---|---|---|---|---|---|
| 100 | 46% | 71% | 90% | 100% | |
| 101 | 37% | 60% | 79% | | 100% |
| 102 | 48% | 76% | 89% | 100% | |
| 103 | 44% | 77% | 90% | 100% | |
| 104 | 41% | 67% | 80% | | 100% |

It was very surprising to the inventors that the in vitro dissolution time was 5 minutes longer when xanthan gum was added to the formulation.

Example 30

In Vivo Dissolution Profile

TABLE 12

Lozenge samples were tested for dissolution according to Example 24. The value indicates weight % of cannabinoid released from the lozenge sample.
Dissolution profile - CBD released from the tablet over time

| Sample | 3 min. | 5 min. | 7.5 min. | 8.5 min. |
|---|---|---|---|---|
| 100 | 60% | 86% | 100% | |
| 101 | 43% | 64% | | 100% |

Example 31

Hardness of Lozenges Versus Dissolution Time

The tablet hardness and dissolution time was evaluated based on sample 102.

TABLE 13

| Tableting force, breaking point and dissolution was measured. | | |
| --- | --- | --- |
| Tableting force [kN] | Tablet break point [N] | Dissolution time [min] |
| 10 | 103 | 16 min |
| 20 | 243 | 16 min |
| 30 | >347 | 16 min |

This result was very surprising since it is conventional within the art of tableting that applying a higher tableting force will result in lower dissolution, i.e. longer dissolution time.

Example 32

Sensorics Evaluation

TABLE 14

| Sensorial test results in accordance with the test set-up of Example 27. | | | | |
| --- | --- | --- | --- | --- |
| Lozenge | Texture | Flavor | Sweetness | Off-notes |
| 109 | ++++ | ++++ | ++++ | ++++ |
| 120 | +++ | ++++ | +++ | ++++ |
| 122 | +++ | +++ | ++ | ++ |
| 124 | +++ | +++ | ++ | +++ |

The invention claimed is:

1. A lozenge composition for controlled release of cannabinoids comprising:
   i) a master granule component consisting of one or more non-dissolved solid particles and one or more cannabinoids dissolved in a lipid carrier that is adsorbed to a surface of the one or more non-dissolved solid particles; and
   ii) an extragranular component comprising one or more extragranular water-soluble ingredients,
   wherein the master granule component is present in a mixture with the extragranular component in the lozenge composition, and
   wherein the one or more non-dissolved solid particles are selected from one or more sugars or one or more sugar alcohols.

2. The lozenge composition according to claim 1, wherein the one or more sugar alcohols are selected from the group consisting of xylitol, lactitol, sorbitol, maltitol, erythritol, isomalt and mannitol, and mixtures and combinations thereof.

3. The lozenge composition according to claim 1, wherein the one or more sugars are selected from the group consisting of dextrose, sucrose, maltose, fructose, lactose, and mixtures and combinations thereof.

4. The lozenge composition according to claim 1, wherein the master granule component is a premixture of the one or more non-dissolved solid particles and the one or more cannabinoids, the one or more cannabinoids being applied to the surface of the one or more non-dissolved solid particles by means of spraying.

5. The lozenge composition according to claim 1, wherein the lozenge composition does not comprise a polymer carrier for the one or more cannabinoids.

6. The lozenge composition according to claim 1, wherein the one or more non-dissolved solid particles are agglomerated to form granules comprising the one or more cannabinoids.

7. The lozenge composition according to claim 1, wherein the lipid carrier comprises one or more terpenes.

8. The lozenge composition according to claim 1, wherein a weight ratio of the one or more cannabinoids relative to the one or more non-dissolved solid particles is from 1:30 to 1:1.

9. The lozenge composition according to claim 1, wherein the one or more non-dissolved solid particles of the master granule component have a volume weighted mean diameter of 10-400 μm.

10. The lozenge composition according to claim 1, wherein the one or more cannabinoids is selected from the group consisting of cannabidiol (CBD), cannabidiolic acid (CBDA), cannabidivarin (CBDV), and mixtures and combinations thereof.

11. The lozenge composition according to claim 1, wherein the one or more cannabinoids is selected from the group consisting of tetrahydrocannabinol (THC), tetrahydrocannabinolic acid (THCA), tetrahydrocannabivarin (THCV), and mixtures and combinations thereof.

12. A powder composition for controlled release of cannabinoids comprising:
   i) a master granule component consisting of one or more non-dissolved solid particles and one or more cannabinoids dissolved in a lipid carrier that is adsorbed to a surface of the one or more non-dissolved solid particles; and
   ii) an extragranular component comprising one or more extragranular water-soluble ingredients,
   wherein the master granule component is present in a mixture with the extragranular component in the powder composition, and
   wherein the one or more non-dissolved solid particles are selected from one or more sugars or one or more sugar alcohols.

13. The powder composition according to claim 12, wherein a weight ratio of the master granule component relative to the extragranular component is from 1:30 to 1:2.

14. The powder composition according to claim 12, wherein the one or more non-dissolved solid particles comprises one or more sugar alcohols in an amount of 5 to 40% by weight of the powder composition and the one or more extragranular water-soluble ingredients comprises one or more sugar alcohols in an amount of 60 to 95% by weight of the of the powder composition.

15. A lozenge composition for controlled release of cannabinoids comprising;
   i) a master granule component premixture consisting of one or more non-dissolved solid particles and one or more cannabinoids adsorbed to a surface of the one or more non-dissolved solid particles; and
   ii) an extragranular component comprising one or more extragranular water-soluble ingredients,
   wherein the master granule component is present in a mixture with the extragranular component in the lozenge composition,
   wherein the one or more non-dissolved solid particles are selected from one or more sugars or one or more sugar alcohols, and
   wherein a weight ratio of the master granule component premixture relative to the extragranular component is from 1:30 to 1:2.

16. The lozenge composition according to claim 15, wherein the weight ratio of the master granule component premixture relative to the extragranular component is from 1:20 to 1:3.

17. The lozenge composition according to claim 15, wherein the one or more cannabinoids are applied in a layer to the surface of the one or more non-dissolved solid particles comprised in the master granule component premixture before blending with the extragranular component.

18. The lozenge composition according to claim 15, wherein the lozenge composition does not comprise a polymer carrier for the one or more cannabinoids.

19. The lozenge composition according to claim 15, wherein the one or more cannabinoids comprises at least one isolated cannabinoid.

20. The lozenge composition according to claim 15, wherein the one or more non-dissolved solid particles comprises one or more sugar alcohols in an amount of 5 to 40% by weight of the powder composition and the one or more extragranular water-soluble ingredients comprises one or more sugar alcohols in an amount of 60 to 95% by weight of the of the lozenge composition.

21. The lozenge composition according to claim 15, wherein the one or more non-dissolved solid particles comprises one or more sugar alcohols in an amount of 20 to 40% by weight of the powder composition and the one or more extragranular water-soluble ingredients comprises one or more sugar alcohols in an amount of 60 to 80% by weight of the of the lozenge composition.

22. The lozenge composition according to claim 15, wherein the one or more non-dissolved solid particles are selected from the group consisting of xylitol, lactitol, sorbitol, maltitol, erythritol, isomalt and mannitol, and mixtures and combinations thereof.

23. The lozenge composition according to claim 15, wherein the one or more cannabinoids is selected from the group consisting of cannabidiol (CBD), cannabidiolic acid (CBDA), tetrahydrocannabinol (THC), tetrahydrocannabinolic acid (THCA), cannabigerol (CBG), cannabichromene (CBC), cannabinol (CBN), cannabielsoin (CBE), iso-tetrahydrocannabinol (iso-THC), cannabicyclol (CBL), cannabicitran (CBT), cannabivarin (CBV), tetrahydrocannabivarin (THCV), cannabidivarin (CBDV), cannabichromevarin (CBCV), cannabigerovarin (CBGV), cannabigerol monomethyl ether (CBGM), and mixtures and combinations thereof.

* * * * *